United States Patent
Nagarkar et al.

(10) Patent No.: US 10,338,029 B2
(45) Date of Patent: Jul. 2, 2019

(54) SYSTEMS AND METHODS FOR IMPROVED PHYSIOLOGICAL MONITORING

(71) Applicant: General Electric Company, Schnectady, NY (US)

(72) Inventors: Kaustubh Ravindra Nagarkar, Clifton Park, NY (US); Jeffrey Michael Ashe, Gloversville, NY (US); William Hullinger Huber, Niskayuna, NY (US); Aaron Judy Couture, Niskayuna, NY (US); Ashraf Said Atalla, Clifton Park, NY (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 994 days.

(21) Appl. No.: 14/565,784

(22) Filed: Dec. 10, 2014

(65) Prior Publication Data

US 2016/0169838 A1  Jun. 16, 2016

(51) Int. Cl.
*A61B 5/05* (2006.01)
*G01N 27/74* (2006.01)
(Continued)

(52) U.S. Cl.
CPC ............. *G01N 27/74* (2013.01); *A61B 5/021* (2013.01); *A61B 5/024* (2013.01); *A61B 5/0205* (2013.01);
(Continued)

(58) Field of Classification Search
None
See application file for complete search history.

(56) References Cited

U.S. PATENT DOCUMENTS 5,794,622 A * 8/1998 Chopp ................. A61B 5/0265
600/431
6,027,946 A  2/2000 Weitschies et al.
(Continued)

FOREIGN PATENT DOCUMENTS

WO  0176656 A2  10/2001
WO  03062794 A2  7/2003
(Continued)

OTHER PUBLICATIONS

Cannata et al., "Development of a Flexible Implantable Sensor for Postoperative Monitoring of Blood Flow", J Ultrasound Med, vol. No. 31, Issue No. 11, pp. 1795-1802, Nov. 2012.
(Continued)

*Primary Examiner* — Jonathan Cwern
(74) *Attorney, Agent, or Firm* — Fletcher Yoder, P.C.

(57) ABSTRACT

A system and method for monitoring a subject are presented. The system includes a sensing device including at least one magnetic source to generate a magnetic field and an array of magnetic sensors disposed within the magnetic field. The sensor array obtains a plurality of magnetic field measurements at a plurality of locations along a vessel carrying a fluid including one or more magnetic particles. Further, the system includes a processing subsystem communicatively coupled to the sensing device, where the processing subsystem determines variations in the measurements caused by magnetization-relaxation of the magnetic particles based on a coupled model that defines behavior of the fluid in the varying magnetic field based on principles of magnetization-relaxation, bulk motion of the magnetic particles towards a determined gradient of the magnetic field, magnetostatics, and conservation of momentum. The processing subsystem estimates values of one or more desired parameters based on the determined variations.

21 Claims, 8 Drawing Sheets

(51) Int. Cl.

| | | |
|---|---|---|
| *A61B 5/021* | (2006.01) | |
| *A61B 5/024* | (2006.01) | |
| *A61B 5/0265* | (2006.01) | |
| *A61B 5/029* | (2006.01) | |
| *A61B 5/145* | (2006.01) | |
| *G01F 1/56* | (2006.01) | |
| *A61B 5/0205* | (2006.01) | |
| *A61B 8/08* | (2006.01) | |
| *G01N 33/18* | (2006.01) | |
| *G01N 33/22* | (2006.01) | |
| *G01N 33/26* | (2006.01) | |
| *G01N 33/49* | (2006.01) | |
| *G01R 33/09* | (2006.01) | |
| *G01F 1/712* | (2006.01) | |
| *A61B 5/00* | (2006.01) | |

(52) U.S. Cl.
CPC ............ *A61B 5/029* (2013.01); *A61B 5/0265* (2013.01); *A61B 5/05* (2013.01); *A61B 5/0515* (2013.01); *A61B 5/14542* (2013.01); *A61B 8/488* (2013.01); *G01F 1/56* (2013.01); *G01F 1/712* (2013.01); *G01N 33/18* (2013.01); *G01N 33/225* (2013.01); *G01N 33/26* (2013.01); *G01N 33/49* (2013.01); *G01N 33/4925* (2013.01); *G01R 33/096* (2013.01); *A61B 5/02416* (2013.01); *A61B 5/6824* (2013.01); *A61B 2562/043* (2013.01)

(56) References Cited

U.S. PATENT DOCUMENTS

| | | |
|---|---|---|
| 6,480,111 B2 | 11/2002 | Canady et al. |
| 8,180,427 B2 | 5/2012 | Phua et al. |
| 8,246,547 B2 | 8/2012 | Phua et al. |
| 8,473,059 B2 | 6/2013 | Tass et al. |
| 2005/0059869 A1 | 3/2005 | Scharf et al. |
| 2006/0264715 A1 | 11/2006 | Mir et al. |
| 2007/0231393 A1* | 10/2007 | Ritter .................. A61K 9/0009 424/489 |
| 2008/0261261 A1 | 10/2008 | Grimes et al. |
| 2009/0203988 A1* | 8/2009 | Phua ..................... A61B 5/024 600/409 |
| 2010/0066363 A1 | 3/2010 | Brazdeikis et al. |
| 2011/0093243 A1* | 4/2011 | Tawhai ............... G06F 17/5018 703/2 |
| 2013/0091941 A1* | 4/2013 | Huh .................... E21B 47/1015 73/152.08 |
| 2015/0105630 A1* | 4/2015 | Kummerl ........... A61B 5/02438 600/301 |
| 2015/0112168 A1* | 4/2015 | Conrad ................ A61B 5/7228 600/309 |
| 2016/0095536 A1* | 4/2016 | Lorraine ................ A61B 5/062 600/424 |

FOREIGN PATENT DOCUMENTS

| | | |
|---|---|---|
| WO | 2006086529 A2 | 8/2006 |
| WO | 2011080191 A1 | 7/2011 |

OTHER PUBLICATIONS

Atalla et al., "Modeling the Magnetic Disturbance of Pulsatile Blood Flow in a Static Magnetic Field", Engineering in Medicine and Biology Society (EMBC), 2014 36th Annual International Conference of the IEEE, Chicago, pp. 1406-1409, Aug. 26-30, 2014.

PCT Search Report and Written Opinion issued in connection with corresponding Application No. PCT/US2015/063180 dated Feb. 16, 2016.

* cited by examiner

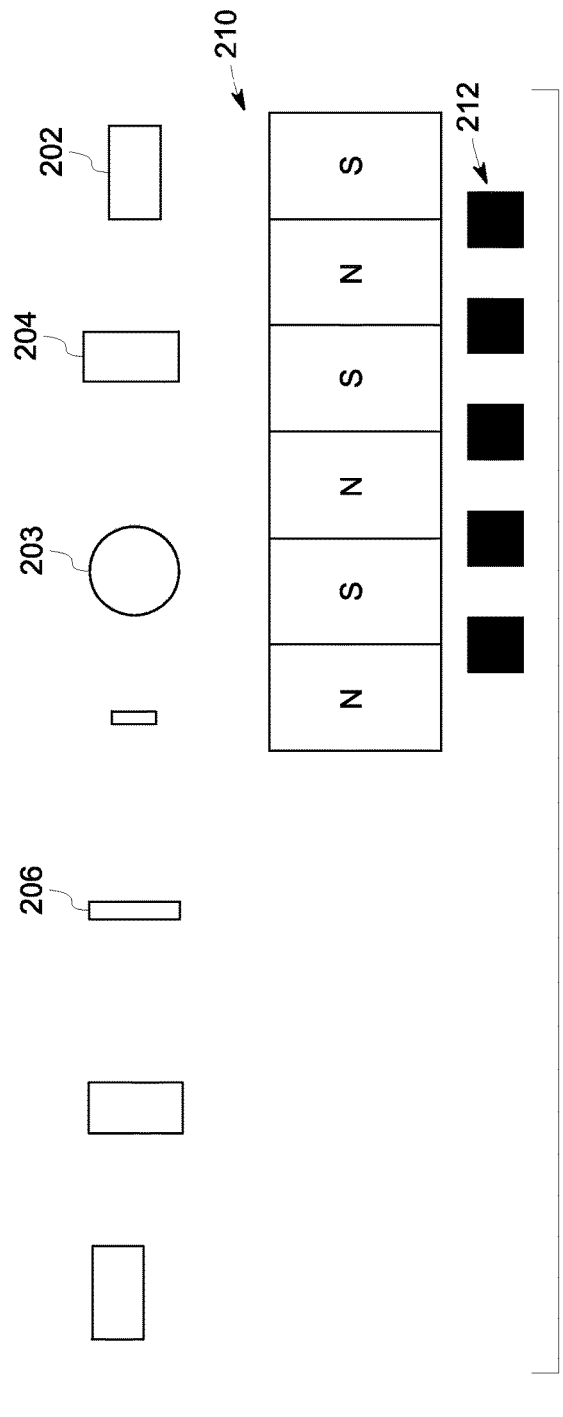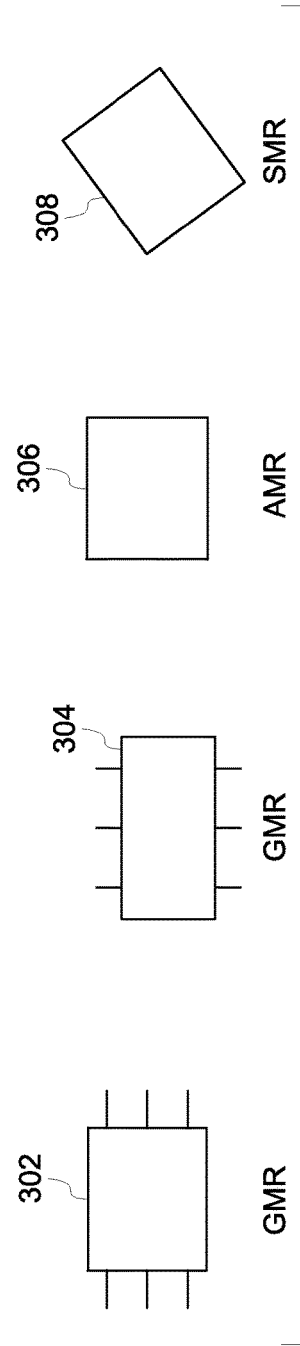

SYSTEMS AND METHODS FOR IMPROVED PHYSIOLOGICAL MONITORING

BACKGROUND

Embodiments of the present specification relate generally to physiological monitoring, and more particularly to systems and methods for enhanced estimation of physiological parameters using an array of magnetic sensors.

Continual monitoring of a patient's physiological parameters such as vital signs and/or blood flow characteristics allows for early detection of physiological anomalies, thus providing timely alerts for life saving interventions. Particularly, routine use of multi-parameter monitors in trauma, surgery, and intensive-care unit settings has greatly improved medical outcomes in recent times. By way of example, pulse oximeters, ultrasonic flow meters, and pressure cuff sensors are routinely used for monitoring oxygen saturation (SpO2), cardiac output, and/or blood pressure to aid in detection of life-threatening medical conditions such as arterial hypoxemia, hypovolemia, and/or internal bleeding. However, such conventional physiological monitoring devices are often too large and/or are prohibitively expensive for routine use outside hospitals.

Accordingly, certain portable electrical, mechanical, and optical monitoring devices have been developed to allow for non-invasive monitoring of physiological parameters of patients. Some of these devices, for example, may be implemented in chest stripes, socks attachments, wristwatches, or finger attachments that may be operatively coupled to a patient. However, use of these portable devices entails direct skin contact, complicated processing, insufficient monitoring capabilities, considerable power consumption, and/or need for a trained operator. Furthermore, measurements made using the conventional devices are highly susceptible to motion artifacts caused by patient motion and/or ambient vibrations.

Certain other conventional monitoring methods propose use of miniature and low-powered magnetic sensors to detect a modulated magnetic signature of blood (MMSB) for use in heart rate, blood flow, and pressure monitoring. In these conventional methods, a magnetic sensor is positioned proximal a target region such as a patient's forefinger to continually measure a uniform magnetic field generated by a permanent magnet placed in the vicinity. The magnetic field measurements, in turn, may be used to determine certain physiological parameters such as flow velocity and arterial distention corresponding to the patient based on an empirical model.

Although such empirical models attempt to correlate the magnetic field measurements to certain physiological parameters, the empirical models do not account for certain magnetic properties such as magnetization relaxation of the blood. Furthermore, the empirical models fail to provide an accurate representation of the blood flow, geometry, and magnetic interaction between the blood and the generated magnetic field. Since these conventional models disregard effects of certain magnetic properties of blood on the magnetic field measurements, values of the physiological parameters determined using such conventional monitoring methods may be inaccurate, and thus, unsuitable for clinical use.

BRIEF DESCRIPTION

In accordance with aspects of the present specification, a system, method and a non-transitory computer readable medium that stores instructions executable by one or more processors to perform a method for monitoring a subject are presented. The system includes a sensing device including at least one magnetic source to generate a magnetic field and an array of magnetic sensors disposed within the magnetic field. The array of magnetic sensors obtains a plurality of measurements corresponding to the magnetic field at a plurality of locations along a vessel including a fluid that has one or more magnetic particles. Further, the system includes a processing subsystem communicatively coupled to the sensing device. The processing subsystem determines variations in the measurements caused by magnetization-relaxation of the magnetic particles in the fluid based on a coupled model that defines behavior of the fluid in the varying magnetic field based on principles of magnetization-relaxation, bulk motion of the magnetic particles in the fluid towards a determined gradient of the magnetic field, magnetostatics, and conservation of momentum. Subsequently, the processing subsystem estimates values of one or more desired parameters based on the determined variations.

DRAWINGS

These and other features, aspects, and advantages of the present disclosure will become better understood when the following detailed description is read with reference to the accompanying drawings in which like characters represent like parts throughout the drawings, wherein:

FIG. 2 is a schematic representation of exemplary orientations of different magnetic sources for use in the monitoring system of FIG. 1;

FIG. 3 is a schematic representation of exemplary orientations of magnetic sensors for use in the monitoring system of FIG. 1;

DETAILED DESCRIPTION

The following description presents systems and methods for enhanced monitoring of physiological parameters of a patient. Particularly, certain embodiments illustrated herein describe easy to use, non-invasive, small footprint, low-weight, ruggedized, and low-power monitoring systems and methods. Embodiments of the monitoring systems and methods employ a varying magnetic field and an array of magnetic sensors for monitoring physiological parameters of the patient with improved accuracy. Specifically, the embodiments described herein present a wearable patient monitor suitable for tracking a medical condition of the patient and/or for providing continual assessment of an effect of medication, exercise, and lifestyle changes on the patient in real-time in a hospital, clinic, home, and/or ambulatory setting.

Additionally, embodiments of the present system and method also provide a three-dimensional (3D) coupled mathematical model that accurately defines relationships between flow of a fluid, magnetization, and magnetic sensing. The accurately defined relationships allow efficient correlation of acquired magnetic response signals with one or more pathological conditions, thereby allowing for a more informed clinical diagnosis and/or efficient treatment planning.

For clarity, embodiments of the present systems and methods are discussed with reference to accurately determining physiological parameters, such as blood flow, blood pressure, and blood oxygenation (SpO2) levels based on an accurate assessment of acquired magnetic response signals using the coupled model. However, certain embodiments of the present systems and methods may also find use in other medical and/or non-medical applications such as non-destructive testing applications. For example, certain embodiments of the present methods and systems may be used in modeling other magnetic fluids for use in detecting cracks in oil and gas pipelines and detecting bearing wear. An exemplary environment that is suitable for practicing various implementations of the present system is described in the following sections with reference to FIG. 1.

Figure 1:
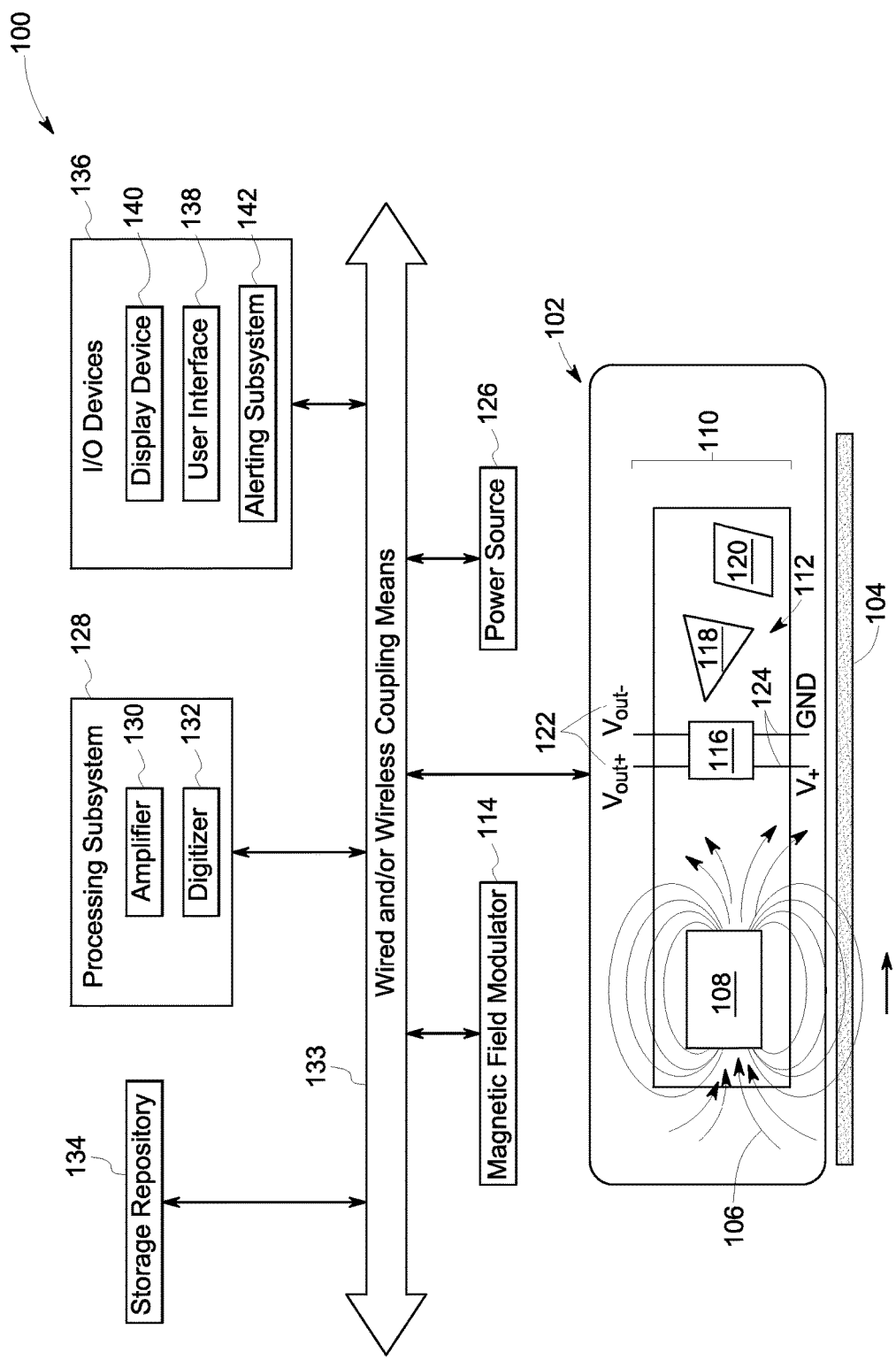
FIG. 1 is a block diagram illustrating an exemplary monitoring system, in accordance with aspects of the present specification.

FIG. 1 illustrates an exemplary monitoring system 100 for use in monitoring a subject such as a patient in real-time. For clarity, the system 100 is described with reference to non-invasive monitoring of physiological parameters such as heart rate, blood flow, and/or arterial blood pressure corresponding to the patient. However, other physiological parameters such as blood oxygenation, stroke volume, arterial stiffness, arterial distention, and hemoglobin content may be similarly determined using the system 100. Furthermore, in certain embodiments, the system 100 may be communicatively coupled to other monitoring systems such an a blood oxygenation monitor, a Doppler ultrasound system, and/or an optical heart rate monitor, for example, to allow for estimation of blood oxygenation and/or other blood flow anomalies. Alternatively, as previously noted, some embodiments of the system 100 may also be used for determining flow characteristics during non-medical monitoring applications.

In a presently contemplated embodiment, the system 100 may be configured to determine the physiological parameters of the patient based on measurement of magnetic field in a vicinity of the blood flow that is indicative of at least blood flow velocity or flow volume at surface arteries in one or more target regions in the subject. Particularly, the system 100 may determine accurate blood flow characteristics from the magnetic field measurements based on a coupled mathematical model. According to certain aspects of the present specification, the coupled model is computed to accurately define one or more relationships between blood flow, magnetization, and the magnetic field measurements to allow for more efficient design of the monitoring system 100, its placement, and assessment of the measured magnetic response signal. Further, in one embodiment, use of the coupled model may aid in identifying and correlating one or more distinct characteristics of the measured magnetic response signal with one or more physiological parameters to identify a pathological condition of the patient.

To that end, in certain embodiments, the system 100 includes a sensing device 102 positioned in contact with, or in proximity of the target regions in the patient to determine one or more clinically useful indications corresponding to the pathological condition of the patient. The target regions, for example, may correspond to a finger, wrist, ankle, and/or head region in the patient. Generally, the target regions may include a blood vessel 104 that transports blood having one or more magnetic particles such as iron carrying compounds to different parts of the patient's body. In one embodiment, identifying a behavior of the blood flowing in the blood vessel 104 under influence of an external magnetic field 106 may aid in determining the clinically useful indications.

Accordingly, in certain embodiments, the sensing device 102 includes at least one magnetic source 108 configured to generate the magnetic field 106 having a desired magnitude and/or direction in the vicinity of the blood vessel 104. To that end, the magnetic source 108, for example, includes a permanent magnet, an electromagnet, and/or a coil of wire. Further, the sensing device 102 includes an array of magnetic sensors 110 ("magnetic sensor array 110") disposed on a substrate 112 for use in measuring changes in the magnetic field 106 due to the pulsatile flow of blood through the blood vessel 104.

Particularly, in certain embodiments, the sensing device 102 may be configured to generate an output voltage signal representative of the changes in the magnetic field 106 measured by the magnetic sensor array 110. However, the output signal may be distorted by external magnetic fields, ambient vibrations, and/or patient movement such as movement of wrist and/or toes. Accordingly, in certain embodiments, the sensing device 102 may further include a magnetic field modulator 114 such as a transmission coil that is configured to modulate the magnetic field 106 generated by the magnetic source 108. Particularly, in one embodiment, the modulator 114 modulates the magnetic source 108 such that the generated magnetic field 106 varies in a time domain and/or a spatial domain. Use of the varying magnetic field 106 aids in matching the response signal received from the magnetic sensor array 110 to the varying magnetic field 106, thereby reducing noise and/or improving a signal-to-noise ratio (SNR) of measurements determined by the magnetic sensor array 110. The lowered noise achieved via use of the varying magnetic field 106 results in fewer motion artifacts, thus providing a robust system for monitoring the physiological parameters of the patient.

Particularly, in certain embodiments, simultaneous measurements of the magnetic field 106 at a plurality of locations using the magnetic sensor array 110 may provide information that may be cohesively used to determine even complex physiological parameters such as blood oxygenation and stroke volume. In one embodiment, the simultaneous measurements may be obtained by one or more magnetic sensors 116, 118, and 120 disposed in the magnetic sensor array 110 at different distances from the magnetic source 108. The magnetic sensors 116, 118, and 120, for example, may include one or more giant magnetoresistance (GMR) sensors, semiconductor magnetoresistance (SMR) sensors, anisotropic magnetoresistance (AMR) sensors, tunneling magnetoresistance (SMR) sensors, and/or any other suitable magnetic sensors.

In certain embodiments, the sensing device 102 may employ different configurations of the magnetic source 108 and the magnetic sensors 116, 118, and 120 suitable for determining accurate magnetic field measurements. Particularly, in one embodiment, the sensing device 102 may include different configurations of the magnetic source 108 and the magnetic sensors 116 that aid in determining an effect of the different configurations and the pulsatile blood flow on magnetic field measurements at different spatial locations. Certain exemplary embodiments of the magnetic source 108 and the magnetic sensors 116, 118, and 120 for use in the sensing device 102 are depicted in FIGS. 2-3.

Particularly, FIG. 2 depicts certain exemplary shapes, sizes, and/or orientations of different magnetic sources for use in the system 100 of FIG. 1. In one embodiment, the magnetic source may correspond to a rectangular magnet 202 that has a size of about 10 millimeters (mm) by about 5 mm. Further, the magnet 202 may be disposed in a horizontal orientation with respect to a longitudinal axis of a blood vessel of interest such that corresponding poles of the magnet 202 are located on top and bottom faces of the magnet 202. In another embodiment, the magnetic source may include one or more rectangular magnets 204 and 206 having different sizes. The magnets 204 and 206, for example, may be disposed in a vertical orientation and/or at a desired angle corresponding to the longitudinal axis of the blood vessel. Alternatively, the magnetic source may include a circular magnetic source 208 configured to generate a varying magnetic field in a vicinity of the blood vessel of the patient. In certain further embodiment, the system 100 includes the magnetic source 210 having interlaced north and south poles. The interlaced poles allow the magnetic source 210 to produce large field gradients. Accordingly, in one embodiment, a plurality of SMR sensors 212 positioned proximal to the magnetic source 210 may be configured to sense locations corresponding to the greatest demagnetization of blood caused by the large field gradients.

Although, FIG. 2 depicts only a few shapes, sizes, and/or orientations of the magnetic source, different combinations of the depicted magnetic sources and/or other suitable shapes and sizes of magnetic sources may find use in the system 100 to generate the varying magnetic field 106 having a desired magnitude, direction, and/or frequency.

Further, FIG. 3 illustrates certain exemplary types, sizes, and/or orientations of different magnetic sensors for use in the system 100 of FIG. 1. For example, the magnetic sensors may include a GMR sensor 302 that may be positioned in parallel to a direction of blood flow in a blood vessel. Alternatively, the magnetic sensor may include a GMR sensor 304 positioned vertically with reference to the direction of blood flow. Further, in certain embodiments, the magnetic sensor may include an AMR sensor 306 and/or an SMR sensor 308 positioned parallel to or at an angle to the direction of the blood flow. In certain embodiments, the magnetic sensors 302, 304, 306 and 308 may include one or more input and/or output leads, for example, to receive a power supply and/to allow for measurement of a corresponding output signal.

Although, FIG. 3 depicts only a few configurations of magnetic sensors, certain other embodiments may employ further types, sizes and/or orientation of magnetic sensors. For example, in one embodiment, the magnetic sensors may include a plurality of SMR sensors 310 having a size of about 1 mm by 1 mm and configured to operate without use of an external power supply. Use of the SMR sensor may provide a larger output signal that is indicative of an extent of blood magnetization and/or demagnetization of the blood due to the magnetic field. Additionally, use of the SMR sensor may also aid in determining magnetic field measurements with a lower noise floor as compared to other magnetoresistance sensors. Specifically, the SMR sensors may provide four orders of higher magnitude magnetic fields and ten orders of better sensitivity than conventionally available GMR sensors. Accordingly, in certain embodiments, the SMR sensors may be positioned on top of or proximal to arrays of permanent magnets with interlaced poles, thereby creating sharp magnetic field gradients that reduce field distortion caused by pulsatile blood flow. The reduced field distortions allow for accurate magnetic field measurements, which in turn, may be accurately correlated with values of one or more physiological parameters.

Use of the different magnetic sensors, thus, allows for fabrication of miniature monitors (for example, of about an inch in diameter) that aid in measuring a flow velocity and progression of pulse as it traverses through each sensor-magnet pair. Thus, in one embodiment, flow and pulse wave velocity (both measured in meters per second) may be accurately calculated based on a determined time delay between the pulses across each magnetic sensor and the distance between the magnetic sensors.

With returning reference to FIG. 1, the magnetic source 108 and the magnetic sensors 116, 118, and 120 having different sizes, shapes, orientations, and/or sensitivities may be disposed on the substrate 112 in desired patterns to allow for optimal measurement of one or more magnetic field characteristics. Specifically, a distance between the magnetic source 108 and the magnetic sensors 116, 118, and 120 may be selectively configured based on strength of the magnetic field 108 to allow for optimal magnetic field measurements. For example, when operating the sensing device 102 in the magnetic field 108 having strength of about 1000 Gauss, the magnetic sensors 116, 118, and 120 may be positioned on the substrate 112 at distances of about 5-10 millimeters (mm) from the magnetic source 108. Other suitable configurations of the magnetic sensors 116, 118, and 120 and the magnetic source 108 may be determined for different characteristics of the magnetic field 106 to allow the sensing device 102 to measure variations in the magnetic field 106 due to the pulsatile flow and other magnetic characteristics of blood flowing across the target regions.

Furthermore, in one embodiment, the sensing device 102 may be disposed proximate, for example, at a distance of about 2-15 mm from the target regions for acquiring non-invasive and/or contact-less magnetic field measurements. In an alternative embodiment, however, the sensing device 102 may be positioned in contact with the target regions such as at extremities of the patient and/or the cardiothoracic region for measuring the magnetic field 106 modulated by pulsatile blood flow at a plurality of locations along the blood vessel 104. In certain embodiments, the contact-less or in-contact configuration of the sensing device 102 may be selected so as to allow the magnetic sensors 116, 118, and 120 to measure a varying magnetic field 106 at different relative locations with greater efficiency. Selection of the contact-less or in-contact positioning of the sensing device 102 may also be based on a sensitivity, type, size, relative position, and/or orientation of the magnetic source 108 and/or one or more magnetic sensors 116, 118, and 120 included in the magnetic sensor array 110.

Figure 4:
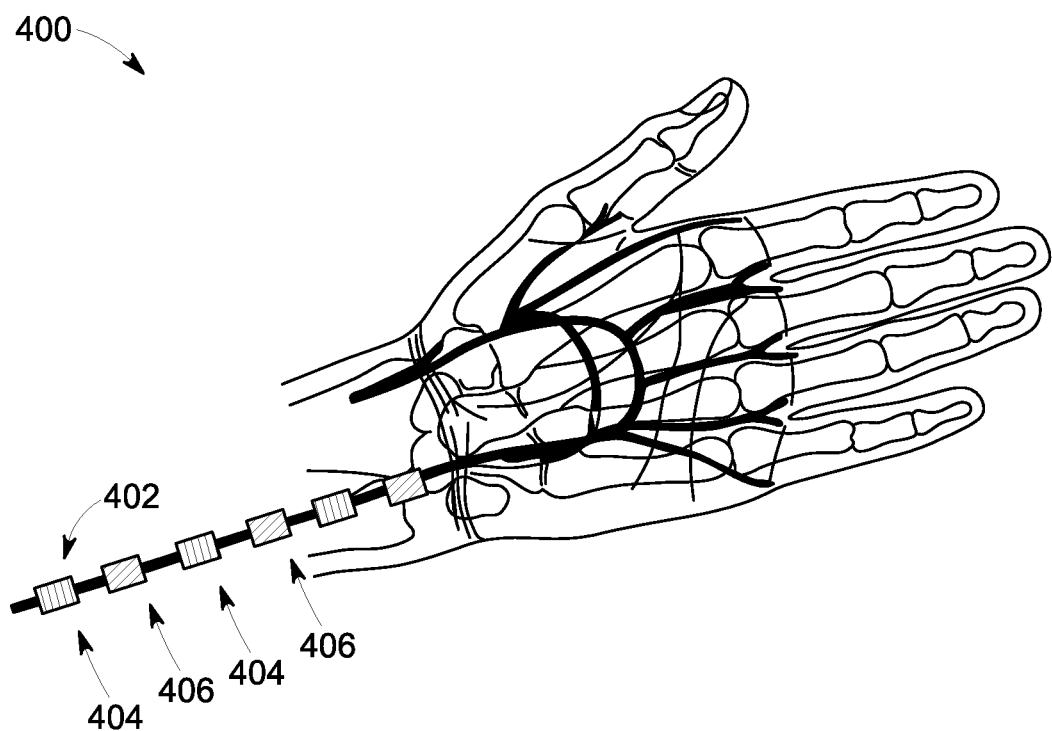
FIG. 4 is a schematic representation of an exemplary array of magnetic sensors for use in the monitoring system of FIG. 1.

FIG. 4, for example, depicts an exemplary sensing device 400 including a magnetic sensor array 402 positioned proximal the wrist of a patient. Specifically, in the embodiment depicted in FIG. 4, the magnetic sensor array 402 includes one or more pairs of a magnetic source 404 and magnetic sensors 406 disposed on a substrate, for example, at a distance of about 5 mm from each other. Further, the magnetic source 404 and the magnetic sensors 406 are positioned linearly at a plurality of spatial locations along the radial and/or ulnar arteries corresponding to the patient. The linearly positioned magnetic source 404 and magnetic sensors 406 allow measurement of magnetic field characteristics at the plurality of spatial locations along the patient's hand. Measuring the magnetic field at the plurality of locations allows acquisition of a larger magnetic response signal that allows for reduced motion artifacts, thus aiding in determining desired blood flow parameters with greater accuracy. For example, the magnetic field measurements obtained at the plurality of locations may aid in determining blood pressure, flow volume, and/or corresponding anomalies corresponding to the patient.

Figure 5:
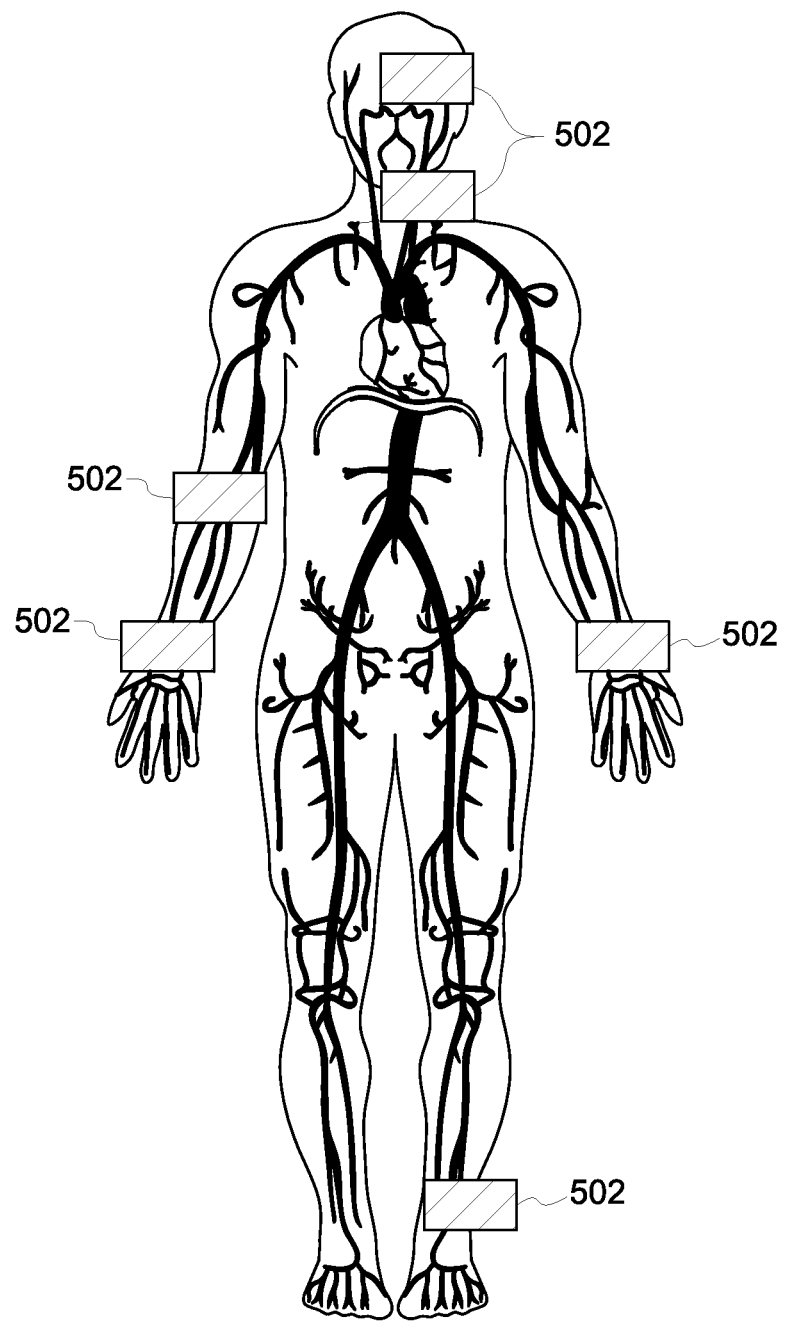
FIG. 5 is a schematic representation of another exemplary array of magnetic sensors for use in the monitoring system of FIG. 1.

Further, FIG. 5 depicts another exemplary sensing device 500 including a magnetic sensor array 502 positioned at or near multiple target regions in a patient. Specifically, the magnetic sensor array 502 may include a plurality of magnetic sensors that may be positioned at a plurality of target regions, such as near the wrists, ankle, cubital fossa, forehead, and/or the neck region of the patient. Simultaneous magnetic field measurements at the plurality of target regions during the same selected time period (for example of about 1 second) provides additional information that may be cohesively used to determine complicated physiological parameters such as anomalous flow characteristics with greater accuracy. The physiological parameters determined from the simultaneous magnetic field measurements, in turn, may be correlated to one or more pathological conditions such as peripheral arterial disease in real time.

By way of example, the simultaneous magnetic field measurements at the wrist and the forehead region may aid in determining an abnormal drop in blood flow volume in carotid and/or cerebral arteries, thus indicating presence of carotid and/or cerebral atherosclerosis. In another example, simultaneous measurement at the wrist and ankle regions may aid in determining differences in blood flow between the wrist and ankle regions, thereby indicating presence of peripheral artery disease. Simultaneous magnetic field measurements at different target regions, thus, may allow a medical practitioner to non-invasively diagnose a complicated health condition and/or prescribe appropriate treatment to the patient in a timely manner.

With returning reference to FIG. 1, the sensing device 102 may be configured to be suitably positioned at the different target regions via the substrate 112. To that end, in one embodiment, the substrate 112 may include a flexible and/or conformable material, such as a polyamide, of a suitable size and shape to allow the sensing device 102 to be positioned on or near a target region to obtain desired magnetic field measurements. In an alternative embodiment, however, the substrate 112 may include a rigid material and/or a combination of rigid and flexible materials that allow the magnetic sensors 116, 118, and 120 to be suitably positioned with respect to the magnetic sensor 106 and the blood vessel 104 for optimal magnetic field measurements.

Further, in certain embodiments, the substrate 112 may include one or more interconnects 122 and 124 configured to operationally couple the magnetic sensors 116, 118, and 120 to one or more other components of the system 100. For example, in one embodiment, the interconnects 122 and 124 may operationally couple the GMR sensor 116 to a power source 126 to receive external power supply for operation and/or to output response signals, respectively. Alternatively, the substrate 112 may include additional circuitry, for example, to interface the SMR sensor 118 that does not require external power supply with other system components. In certain other embodiments, the substrate 112 may further include an additional initialization circuit (not shown) for configuring the AMR sensor 120 for detecting and measuring the varying magnetic field 106.

According to certain aspects of the present specification, the magnetic sensors 116, 118, and 120 may be configured to detect minute variations in the magnetic field 106 and translate the detected variations into a proportional output voltage signal. Accordingly, in one embodiment, the magnetic sensors 116, 118, and 120 may include a thin film of a magnetoresistive material such as Permalloy (nickel-iron) deposited on a silicon substrate and patterned to form a resistive strip. A plurality of such resistors may be connected, for example, in a half or full Wheatstone bridge configuration to provide predictable output voltages when subjected to known magnetic fields. Generally, application of an external magnetic field to the magnetic sensors 116, 118, and 120 causes reorientation of corresponding magnetization vectors leading to variations in a corresponding electrical resistance. The variations in the electrical resistance, in turn, causes generation of output voltages that may be correlated with the minute variations in the magnetic field 106 detected by the corresponding magnetic sensors 116, 118, and 120.

Accordingly, in one embodiment, the magnetic sensors 116, 118, and 120 may be configured to detect the minute variations in the varying magnetic field 106 caused by the pulsatile blood flow through the blood vessel 112. Particularly, the minute variations in the magnetic field 106 may cause a determined potential to be applied, for example, across the interconnects 122 corresponding to the magnetic sensor 116. The applied potential, in turn, causes variation in a corresponding resistance of the magnetic sensor 116, which may be linearly translated to an output voltage signal that may be measured across the interconnects 124. In certain embodiments, the system 100 may be configured to use the measured output signal to quantify the magnetic field variations, for example, for use in detecting one or more pathological conditions corresponding to the patient.

Particularly, in one embodiment, the system 100 may be configured to use a coupled model to accurately determine the physiological parameters based on the measurements obtained by the magnetic sensor 116, 118, and 120. However, unlike conventional magnetic sensing devices that employ a localized, constant, and unidirectional magnetic field, the system 100 is configured to use the varying magnetic field 106 for determining the physiological parameters based on magnetic response signals received from the magnetic sensors 116, 118, and 120. The varying magnetic field 106 causes brief magnetization and demagnetization of blood as it flows under the magnetic field source 108 and magnetic sensor array 104. The demagnetization and pulsatile flow of blood through the blood vessel 112 create minute yet distinctive distortions in the magnetic field 106, in turn, generating a proportional magnetic response signal that may be correlated with one or more pathological conditions in the patient.

Specifically, in certain embodiments, the system 100 may process the magnetic response signal using the coupled model to distinguish between components of the magnetic response signal that correspond to the pulsatile flow of blood and the components that correspond to the magnetization relaxation of blood flowing away from the magnetic source 108.

To that end, in one embodiment, the system 100 includes a processing subsystem 128 configured to process the magnetic response signal to determine clinically useful information. Accordingly, the processing subsystem 112, for example, includes one or more general-purpose or application-specific processors, digital signal processors, microcomputers, microcontrollers, Application Specific Integrated Circuits (ASICs), and/or Field Programmable Gate Arrays (FPGA), and/or other suitable processing devices.

Further, in one embodiment, the processing subsystem 128 may be configured to amplify and/or digitize the output signal measured at different spatial locations along the blood vessel 104. Specifically, in certain embodiments, the processing subsystem 128 may further include an amplifier 130 and a digitizer 132 configured to amplify and digitize the typically low output signal acquired at different spatial locations using different configurations of the magnetic source 108 and the magnetic sensors 116, 118, and 120. Moreover, the processing subsystem 128 may be communicatively coupled to the sensing device 102 via wired and/or wireless coupling means 133 to receive the magnetic response signal. Particularly, the sensing device 102 may include additional electronic circuitry (not shown) such as a wired and/or wireless interface module, transmitter, receiver, encoder, and/or decoder for communicating with the processing subsystem 128 via the wired and/or wireless coupling means 133.

In certain embodiments, the wired and/or wireless coupling means 133, for example, may include one or more electrical cables, magnetic coupling means, and/or electrostatic coupling means. Additionally, the wired and/or wireless coupling means 133 may also include digital communications links such as a backplane or a digital bus, wired communications networks, and/or wireless communications networks. Further, in one embodiment, the wired and/or wireless coupling means 133 may communicatively couple the processing subsystem 128 to additional devices (not shown) such as a picture archiving and communications system (PACS), a remote communication device, and/or a hospital information system (HIS) for determining clinically relevant information from the digitized magnetic response signal.

As previously noted, the processing subsystem 128 may be configured to determine the clinically relevant information such as values of physiological parameters from the digitized output signal using the coupled model. Particularly, use of the coupled model may aid in differentiating between useful and noisy components corresponding to the digitized magnetic response signal, thus allowing for a more efficient determination of the physiological parameters. An embodiment of the coupled model for use by the system 100 to determine the physiological parameters will be described in greater detail with reference to FIGS. 6-7.

Further, in one embodiment, the processing subsystem 128 may be configured to store the determined values of the physiological parameters and/or the digitized magnetic response signal in a storage repository 134. To that end, the storage repository 134, for example, may include a random access memory, a read only memory, a disc drive, solid-state memory device, and/or a flash memory. Additionally, the storage repository 134 may store information and/or executable instructions corresponding to the coupled model for use in determining the physiological parameters and corresponding pathological conditions from the digitized magnetic response signal. In certain embodiments, the storage repository 134 may also store commands and inputs received from an operator for use during a diagnostic procedure.

Accordingly, in one embodiment, the system 100 may include one or more user input-output (I/O) devices 136, such as a keyboard, touchscreen, graphical user interface (GUI) 138, microphone, mouse, buttons, switches, display device 140, audio devices, and/or video devices to receive the operator input and commands. In an exemplary implementation, the I/O devices 136 are operatively coupled to the processing subsystem 128 over the wired and/or wireless coupling means 133 to allow the operator to select one or more target regions and/or imaging parameters, for example, via the GUI 138 on the local or remote display device 140. Additionally, the processing subsystem 128 may be configured to communicate clinical information derived from the digitized magnetic response signal and/or determined values of the physiological parameters to the display device 140 for use in real-time review, diagnosis, analysis, and/or treatment of the patient.

Additionally, in certain embodiments, the processing subsystem 128 may be configured to communicate an audio and/or visual alert message to the I/O devices 136 through an alerting subsystem 142. Specifically, in one embodiment, the processing subsystem 128 may configure the alerting subsystem 142 to communicate the alert message when values of one or more physiological parameters such as blood pressure or volume are outside desirable thresholds. For example, the alerting subsystem 142 may be configured to communicate the alert message via an email, a short messaging service (sms), and/or a popup to a remotely connected system such as the HIS or a selected mobile phone number if the physiological parameter values are outside clinically prescribed, pre-programmed, and/or user-defined thresholds.

Embodiments of the system 100, thus, provide a low power, cuff-less, non-invasive, and portable sensing device for use in continual monitoring of one or more physiological parameters corresponding to the patient. Particularly, use of the magnetic sensor array 110 allows for generation of stronger and redundant output signals to provide higher SNR and improved robustness against stray magnetic fields. Additionally, the arrayed sensor design aids in simultaneous magnetic field measurements at a plurality of locations, thus providing more information that may be cohesively used to determine complex physiological parameters. For example, the information may be used for continuous monitoring of physiological parameters, including blood flow, blood pressure, hemoglobin content, as well as blood oxygen levels that are suitable for early medically austere conditions.

Furthermore, embodiments of the system 100 employ the coupled model for identifying and correlating magnetization and demagnetization delays with changes in blood volume, oxygenation levels, and flow velocity, thereby providing more accurate estimates of the physiological parameters. Certain embodiments of the coupled model that defines relationships between flow of a fluid, magnetization, and magnetic sensing will be described in greater detail with reference to FIG. 6.

Figure 6:
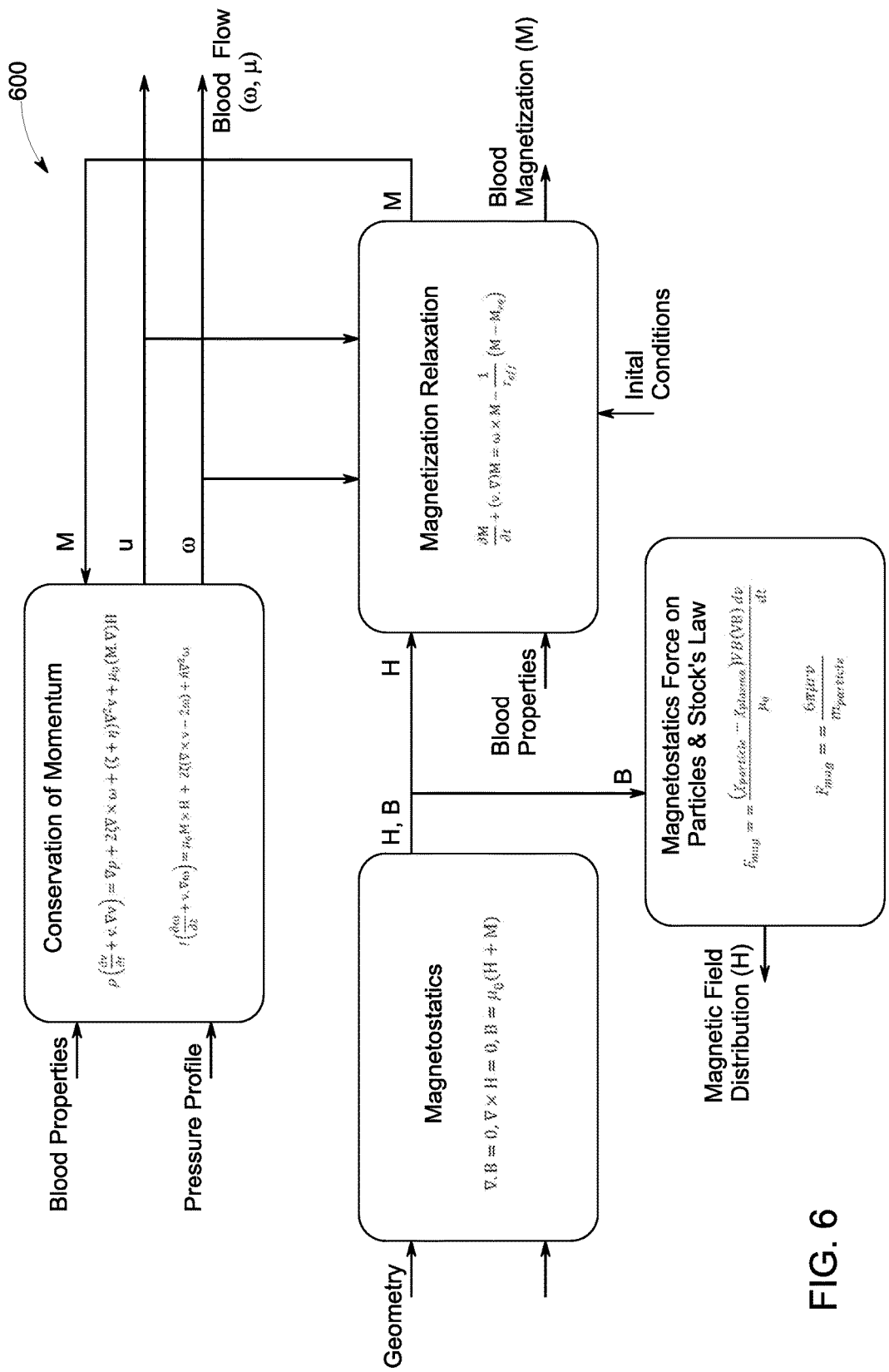
FIG. 6 is a graphical representation of a coupled model that defines relationships between flow, magnetization, and magnetic sensing for use in the monitoring system of FIG. 1.

FIG. 6 depicts a schematic representation 600 of a coupled model for use in the monitoring system of FIG. 1. For clarity, one or more aspects of FIG. 6 will be described in the following description with reference to the components of the monitoring system 100 depicted in FIG. 1.

As previously noted, conventional non-invasive blood flow monitoring systems employ empirical models that attempt to correlate the magnetic field measurements to certain physiological parameters. However, the empirical models do not account for changes in magnetic field disturbances due to varying blood constituents and variable blood flow. Moreover, the empirical models focus on a pulsatile motion of the blood that may be easily corrupted by patient motion, ambient vibrations, and/or magnetic interference due to presence of metallic and/or electronic equipment in vicinity. The empirical models, thus, lack realistic representation of flow, geometry, and magnetic interaction between the blood and a generated magnetic field.

In contrast, embodiments of the present specification employ a coupled model that accurately represents behavior of blood under effect of the magnetic field 106. Particularly, the coupled model represents the behavior of blood based on an embodiment of Navier Stokes equations representative of conservation of momentum, magnetization relaxation, and Maxwell's equations representative of magnetostatics.

Generally, due to the presence of iron carrying compounds in the red blood cells, the blood flowing under the sensing device 102 is magnetized under the influence of the magnetic field 106 generated by the magnetic source 108. Further, the blood is demagnetized while flowing away from the magnetic field 106. This pulsatile flow of blood under the influence of the magnetic field 106 causes minute distortions in the magnetic field 106, which may be measured by the magnetic sensors 116, 118, and 120. Particularly, the magnetic sensors 116, 118, and 120 generate an output signal representative of the measured disturbances, which in turn, may be correlated to one or more physiological parameters.

However, the output signal corresponding to the measured disturbances in the magnetic field 106 may not solely depend upon the pulsatile motion of blood. Particularly, one or more components of the output signal may correspond to the magnetization and/or the demagnetization of blood that may aid in providing a more accurate indication of a relationship between the measured magnetic field disturbances and the physiological parameters. According to certain aspects of the present specification, the coupled model describes an effect of magnetic parameters such as the magnetization and/or the demagnetization of blood and magnetic saturation in view of the conservation of momentum and magnetostatics to accurately represent the behavior of blood, and thereby allowing for determining accurate values of desired physiological parameters.

In particular, FIG. 6 depicts a robust ferrohydrodynamics coupled model (flow-magnetization-sensing) that completely represents a flow interaction of a fluid including magnetic particles with an external magnetic field. According to certain exemplary aspects of the present specification, the interaction between the fluid and the magnetic field may be represented via two main phenomena that were discovered by the inventors to occur when the fluid is in an idle state and when the fluid is under the field effect of a static magnetic field. The two phenomena include magnetization and demagnetization of blood and bulk motion of magnetic particles in the fluid towards the magnetic field gradient.

The magnetization and demagnetization of fluid may be described as follows. In the idle state, the magnetic particles in the fluid, under the field effect, attempt to align their magnetic moments in a direction of a local magnetic field, causing the fluid to be magnetized to a certain extent. Once the magnetized fluid leaves the field effect, the fluid interacts with the static magnetic field causing a distortion of the magnetic field. Particularly, the range of the disturbance in the signal varies in intensity depending on strength of the applied magnetic field as well as magnetic properties of the fluid. Additionally, the fluid magnetization also decays to zero with an effective relaxation time once it leaves the field effect.

Further, the bulk motion of the magnetic particles in the fluid towards magnetic field gradient may be described as follows. In the idle state, the fluid particles cluster toward maximum field gradient points. Once the fluid leaves the field effect, the fluid shows an inhomogeneous concentration due to the dispersion of the fluid, which in turn, affects the magnetic field measured above this concentration profile. Particularly, the fluid particles disperse once they leave the magnetic field region. Accordingly, the magnetic sensors are positioned in close proximity to the magnetic source to utilize the phenomenon of bulk motion.

Generally, the magnetization and demagnetization of fluid depends greatly on the external magnetic field strength and the demagnetization time of the fluid, which at low field densities may be of the order of microseconds. Further, the bulk motion of the magnetic particles depends on an existence of a high magnetic field gradient, which is achievable regardless of the magnetic field strength. According to exemplary aspects of the present specification, the coupled model accounts for both phenomena. Further, in one embodiment, the coupled model defines a feasibility of acquiring each magnetic response signal based on the signal strength and the sensitivity of the magnetic sensors by building a basic coupled model using a single magnet. Additionally, signal strength for each phenomenon is determined. Further, impact of the magnetic field strength and the field gradient on the signal strength is defined based on a sensitivity study. Subsequently, the magnet design (quantity, shape, alignment, etc.) may be adapted to maximize the signal strength and capture the modeled signal for determining physiological parameters with greater accuracy.

Figure 7:
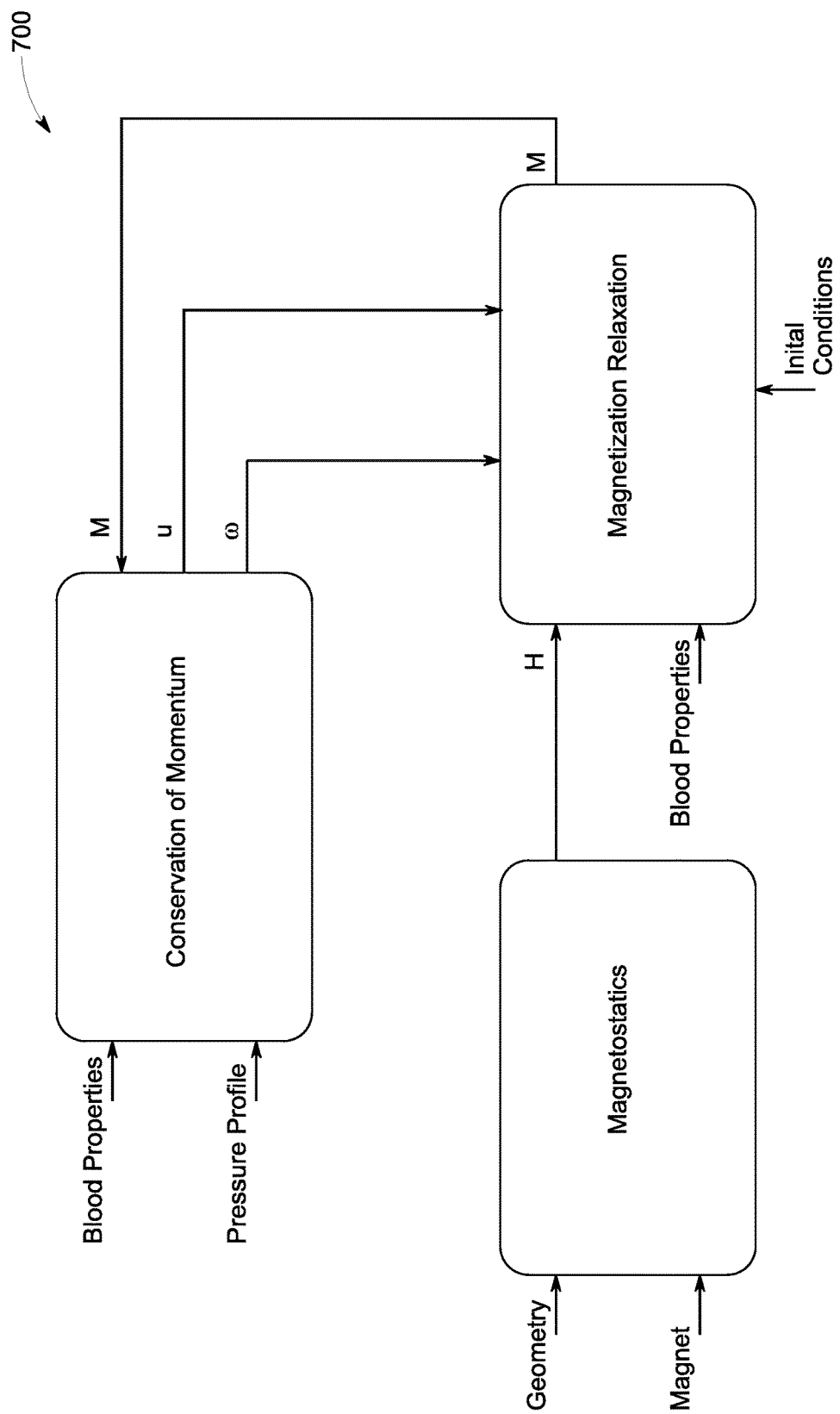
FIG. 7 is a graphical representation of an exemplary implementation of the coupled model that focuses on a selected subset of phenomenon affecting blood flow.

FIG. 7 depicts a graphical representation 700 of an exemplary implementation of the coupled model that focuses on a selected subset of phenomenon affecting blood flow. Particularly, in the coupled model, the conservation of linear and angular momentum may be represented using fluid mechanics equations governing ferrohydrodynamics. Accordingly, the conservation of linear and angular momentum of the blood (or any other magnetic fluid), for example, may be represented using equations (1) and (2):

$$\rho\left(\frac{\partial v}{\partial t} + v \cdot \nabla v\right) = \nabla p + 2\zeta \nabla \times \omega + (\zeta + \eta)\nabla^2 v + F \quad (1)$$

$$I\left(\frac{\partial \omega}{\partial t} + v.\nabla \omega\right) = 2\zeta(\nabla \times v - 2\omega) + \gamma \nabla^2 \omega + T \quad (2)$$

where v corresponds flow velocity of the blood in meters/second, ω corresponds to spin velocity (1/second), p corresponds the pressure in newton/meter$^2$, ρ corresponds to fluid density in kilogram/meter$^2$, η corresponds to dynamic viscosity (Ns/m2), I corresponds to fluid moment of inertia density [kg/m], ζ corresponds to vortex viscosity [Ns/m2], γ corresponds to shear coefficient of spin viscosity [Ns], and F[N] & T[Nm] correspond to body forces and torques per unit volume (magnetic forces and torques in this context) acting on the blood.

Further, the magnetization of blood may be defined as aligning magnetic moments (m) of magnetic particles in the blood along the direction of the local magnetic field in the presence of an external magnetic field. However, such alignment may be impeded due to Brownian relaxation ($\tau_B$) and the Néel mechanism. The Brownian relaxation causes each of the magnetic moments m to rotate with the corresponding magnetic particle, whereas the Néel mechanism causes the magnetic moment m to rotate inside the magnetic particle with a reference time ($\tau_N$) while the magnetic particle itself does not rotate. In one embodiment, a Néel relaxation time constant depends on the magnetic anisotropy energy density. Accordingly, a value of the Néel relaxation time constant changes with the applied magnetic field. Moreover, if the external magnetic field is set to zero, in the coupled model, the blood magnetization M may decay to zero with an effective relaxation time ($\tau_{eff}$), represented using equation (3).

$$\tau_{eff} = \frac{\tau_N \tau_B}{\tau_N + \tau_B} \quad (3)$$

Further, the blood magnetization relaxation may be represented using equation (4).

$$\frac{\partial M}{\partial t} + (v \cdot \nabla) M = \omega \times M - \frac{1}{\tau_{eff}} (M - M_{eq}) \quad (4)$$

where $M_{eq}$ corresponds to equilibrium magnetization [A/m] and is given by the Langevin equation.

Further, the Langevin equation may be represented using equation (5).

$$M_{eq} = M_{sat} \left( \coth(\alpha) - \frac{1}{\alpha} \right) \frac{H}{H} \quad (5)$$

where $M_{sat}$ corresponds to a saturation magnetization of the blood, whereas $\alpha$ corresponds to a fitting parameter that depends on the applied magnetic field and temperature.

According to aspects of the present specification, magnetic properties of the blood influence the output signal received from the magnetic sensors 116, 118, and 120. Particularly, the inventors' determined that the properties that significantly affect the output signal include the relaxation time ($\tau_{eff}$) that corresponds to the time required for magnetization/demagnetization and saturation magnetization ($M_{sat}$) that corresponds to a maximum possible level of blood magnetization. Accordingly, in an exemplary implementation, values corresponding to the relaxation time $\tau_{eff}$ were determined to be dependent on a hematocrit content, oxygenation level, and temperature, whereas the saturation magnetization Msat was determined to be dependent on simulated hemoglobin magnetic susceptibility.

Further, in the coupled model, the magnetic field distribution may be described, for example, using Maxwell's equations defined in equations (6) and (7).

$$\nabla \cdot B = 0 \quad (6)$$

$$\nabla \times H = J \quad (7)$$

where B[T] corresponds to magnetic field density, H corresponds to magnetic field intensity, and J [A/m2] corresponds to a current density.

In one embodiment, the relation between the magnetic field density B and the intensity H may be represented using equations (8)-(11).

$$B = \mu H \quad (8)$$

$$\mu = \mu_0 \mu_r \quad (9)$$

$$M = \chi H \quad (10)$$

$$\mu_r = \chi + 1 \quad (11)$$

where $\mu$ corresponds to the permeability of blood, $\mu_0$ corresponds to the permeability of vacuum, $\mu_r$ corresponds the relative permeability of blood, and $\chi$ corresponds to the magnetic susceptibility of blood.

Here, it may be noted that deoxygenated or venous blood exhibits diamagnetic properties ($\chi<0$) while oxygenated arterial blood exhibits paramagnetic properties ($\chi>0$).

Furthermore, the magnetized blood interacts with the external magnetic field to produce attractive force on each magnetized particle in the blood. Particularly, the magnetic force presents itself as a body force and torque on the blood. Accordingly, the magnetic force and torque on blood per unit volume may be represented, for example, using equations (12) and (13).

$$F = \mu_0 (M \cdot \nabla) H \quad (12)$$

$$T = \mu_0 M \times H \quad (13)$$

where $\mu_0$ corresponds to magnetic permeability of free space, M corresponds to magnetization, and H corresponds to the magnetic field strength.

As evident from equations (12) and (13), the internal magnetic force and torque are proportional to the magnetic field H and blood magnetization M. Accordingly, the internal magnetic force and torque on the blood may be neglected, thus eliminating equation (2). Moreover, upon assuming blood as a non-conducting medium, a simplified system of equations corresponding to the coupled model may be represented using equations (14)-(15).

$$\rho \left( \frac{\partial v}{\partial t} + v \cdot \nabla v \right) = -\nabla p + (\eta) \nabla^2 v \quad (14)$$

$$\frac{\partial M}{\partial t} = \frac{1}{\tau_{eff}} (M - M_{eq}) \quad (15)$$

Further, in one embodiment, the coupling between the magnetic field measurements and the flow systems, for example, may be implemented using a moving mesh technique. The moving mesh technique accounts for magnetization of the blood during idle and flowing states and demagnetization of blood flowing away from the magnetic source 108. Particularly, the magnetization/demagnetization of the blood may be accounted for using equation (15).

In certain embodiments, one or more parameters such as the magnetic susceptibility of deoxygenated and oxygenated blood, blood density, dynamic viscosity, permeability of vacuum, heartbeat frequency, diameter of the blood vessel and magnet diameter are determined from reference values determined from previous clinical and/or experimental implementations. Further, the blood is assumed to be a Newtonian fluid with noslip condition. Moreover, the driving force for the blood flow in a blood vessel is conventionally recognized as the gradient of pressure across the vessel. Accordingly, a pulsatile inlet boundary condition for blood pressure is used at the inlet, while a zero pressure is assigned to the outlet of the blood vessel. Thus, in one embodiment, the inlet pressure pulse may be represented using equation (16).

$$p = p_0 [\sin(2\pi f t)] + \sqrt{\sin(2\pi f t)^2} \quad (16)$$

where $P_0$ corresponds to a reference pressure and f corresponds to the frequency of the heartbeat of the patient.

Further, in certain embodiments, one or more physiological parameters such as velocity of blood flow may be estimated by determining the magnetization-relaxation of blood in presence of an applied magnetic field using equations (3)-(13) and (16). The determined magnetization-relaxation may then be used to determine the blood velocity based on the simplified system of equations defined in equations (14)-(15).

The coupled model, thus, provides an enhanced description of the relationship between the magnetic field measurements and physiological parameters based on certain magnetic properties such as the magnetization relaxation and magnetic saturation of the blood. The enhanced description of the relationship between the magnetic field measurements and physiological parameters, in turn, may be used to optimize the design and operation of wearable devices for efficient physiological monitoring.

In an exemplary implementation, the relationship between the magnetic field measurements, the magnetization-relaxation, and the blood flow defined by the coupled model was validated. Particularly, the magnetic field measurements were obtained by varying a plurality of factors and evaluating behavior of the resulting magnetic field measurements. Certain examples of factors that were varied are listed in Table 1.

TABLE 1

| Factor | Level | Details of Variation |
| --- | --- | --- |
| Magnetic Sensors | 2 | AMR, GMR. SMR |
| Magnetic Source | 2 | Square, Rectangle |
| Magnetic Sensor orientation | 2 | As shown in FIG. 3 |
| Magnetic Source orientation | 4 | As shown in FIG. 2 |
| Distance (magnetic source to magnetic sensors) | 2 | 2-4 centimeters |
| Media | 2 | Blood, Water |
| Pumping Frequency | 3 | 50 bpm, 20 bpm, No flow |

In the exemplary implementation, the magnetic field measurements indicated a shift in the maximum value of the measured magnetic field towards the magnet in lower (20 bpm) and no flow conditions. The different blood flow conditions result in different rates of magnetization and/or demagnetization of the blood. The variation in the rates of magnetization and demagnetization, in turn, causes a corresponding variation in the magnetic field measurements that are obtained at the same location but during different flow conditions.

Figure 8:
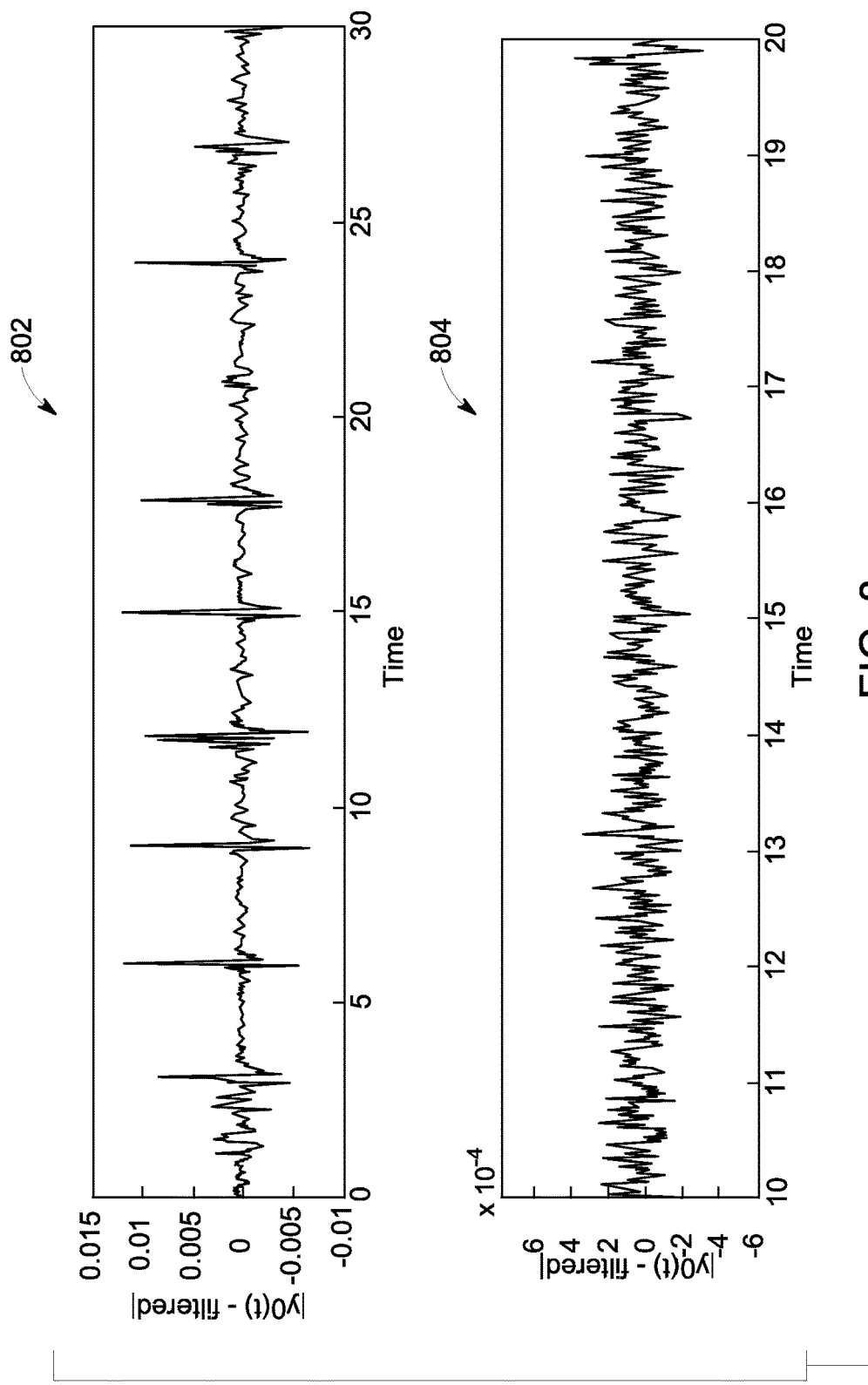
FIG. 8 is a graphical representation of experimental results corresponding to magnetic field measurements in presence and absence of blood flow.

By way of example, FIG. 8 depicts graphical representations 802 and 804 corresponding to exemplary magnetic field measurements obtained by a non-invasive sensor such as the sensing device 102 of FIG. 1 in presence and absence of blood flow, respectively. As shown in the graphical representation 802, a strong output signal with clear maxima and minima values is observed when the magnetic field measurements as obtained in presence of flowing blood. In contrast, the graphical representation 804 depicts a substantially constant signal obtained by the magnetic sensors in absence of blood flow. The depictions of the graphical representations 802 and 804, thus, indicate significance of flow on the magnetic field measurements and a corresponding MMSB. Particularly, as previously noted, the decaying magnetization of the flowing blood causes a noticeable change in the magnetic field measurements obtained in a region proximal to the magnetic sensor as compared to the measurements obtained in regions further away from the magnetic sensor.

According to certain aspects of the present specification, the coupled model may aid in efficiently correlating a change in magnetic field measurements attributable to the demagnetization of blood to one or more physiological parameters such as blood flow, volume, and/or pressure. Continual monitoring of the physiological parameters using the present system and method, in turn, may provide real-time information to a medical practitioner to aid in timely diagnosis and/or treatment for one or more pathological conditions corresponding to the patient. An embodiment of the present method for monitoring physiological parameters of a subject using the system of FIG. 1 is described in greater detail with reference to FIG. 8.

Figure 9:
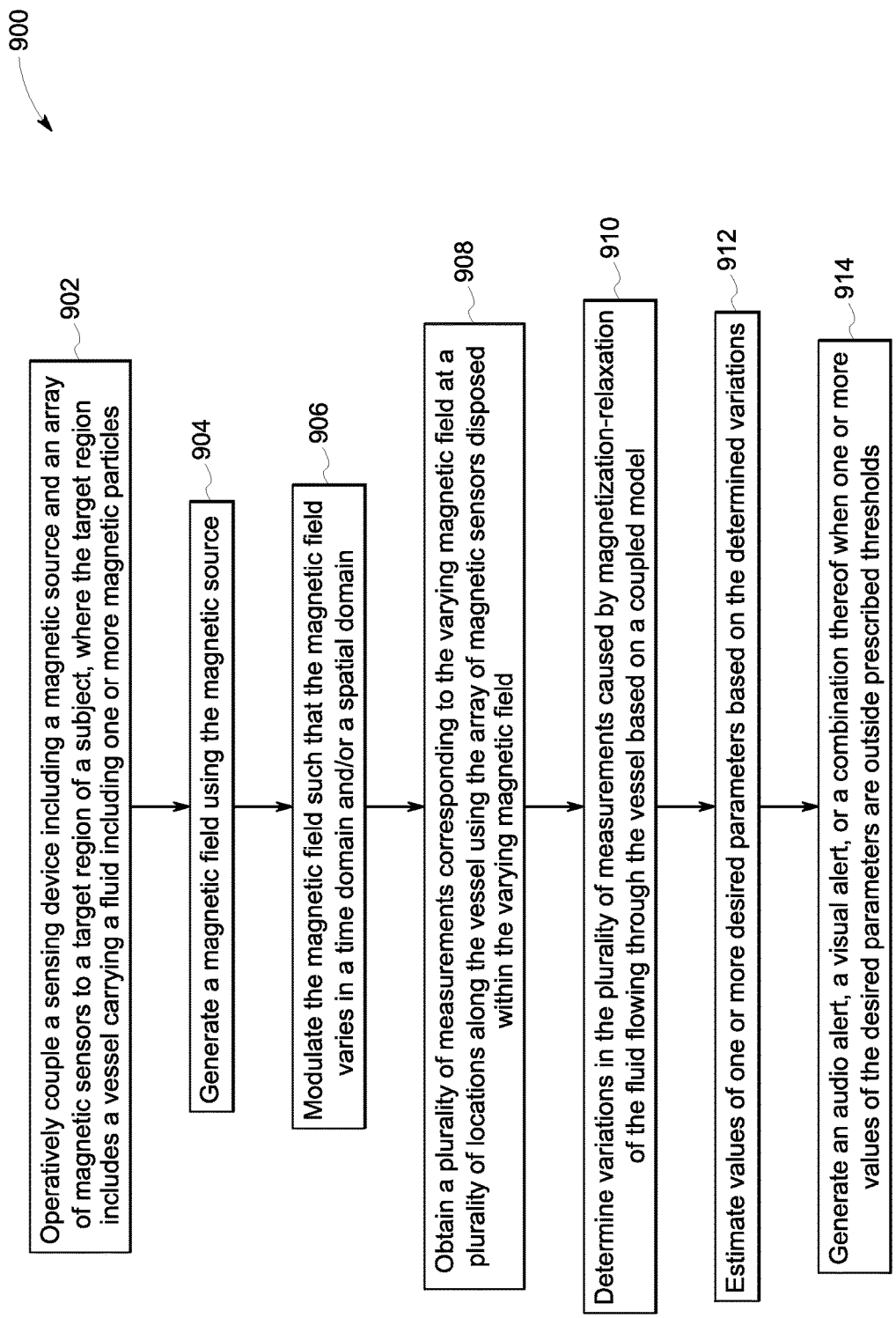
FIG. 9 is a flow diagram illustrating an exemplary method for monitoring physiological parameters, in accordance with aspects of the present specification.

Particularly, FIG. 9 illustrates a flowchart 900 depicting an exemplary method for monitoring physiological parameters corresponding to a subject. The exemplary method may be described in a general context of computer executable instructions stored and/or executed on a computing system or a processor. Generally, computer executable instructions may include routines, programs, objects, components, data structures, procedures, modules, functions, and the like that perform particular functions or implement particular abstract data types. The exemplary method may also be practiced in a distributed computing environment where optimization functions are performed by remote processing devices that are linked through a wired and/or wireless communication network. In the distributed computing environment, the computer executable instructions may be located in both local and remote computer storage media, including memory storage devices.

Further, in FIG. 9, the exemplary method is illustrated as a collection of blocks in a logical flow chart, which represents operations that may be implemented in hardware, software, or combinations thereof. The various operations are depicted in the blocks to illustrate the functions such as modulating the magnetic field, obtaining a plurality of measurements, and estimating values of one or more desired parameters corresponding to the exemplary method. In the context of software, the blocks represent computer instructions that, when executed by one or more processing subsystems, perform the recited operations.

The order in which the exemplary method is described is not intended to be construed as a limitation, and any number of the described blocks may be combined in any order to implement the exemplary method disclosed herein, or an equivalent alternative method. Additionally, certain blocks may be deleted from the exemplary method or augmented by additional blocks with added functionality without departing from the spirit and scope of the subject matter described herein. For discussion purposes, the exemplary method will be described with reference to the elements of the navigation system 100 of FIG. 1. However, the present method may also be used to improve noise rejection in various other medical and/or non-medical systems that employ magnetic sensors.

The method begins at step 902, where a sensing device including a magnetic source and an array of magnetic sensors is operatively coupled to a target region of a subject, where the target region includes a vessel carrying a fluid including one or more magnetic particles. In one embodiment, the fluid corresponds to the blood of a patient flowing through a blood vessel. However, in an alternative embodiment, the fluid may correspond to oil or gas flowing through a pipeline. Moreover, in certain embodiments, the operative coupling may entail positioning the sensing device directly in contact, or above (for example, 1 mm) the vessel carrying the fluid, for example, using a patch or a mechanical means.

Further, at step 904, a magnetic field may be generated using the magnetic source. Particularly, a magnetic field having a desired magnitude and/or direction may be generated, for example, using a permanent magnet, an electromagnet and/or a coil magnet. Additionally, at step 906, the generated magnetic field may be modulated such that the magnetic field varies in a time domain and/or a spatial domain with a desired frequency. Use of the varying magnetic field may aid in matching output signals received from the magnetic sensor array to the varying magnetic field, thereby lowering a noise floor corresponding to determined magnetic field measurements. The lowered noise floor results in fewer motion artifacts, thus providing a robust system for monitoring the physiological parameters.

Moreover, at step 908, a plurality of measurements corresponding to the varying magnetic field may be obtained at a plurality of locations along the vessel using the array of magnetic sensors disposed within the varying magnetic field. Particularly, in one embodiment, two or more of the measurements may be obtained simultaneously. Alternatively, two or more measurements may be determined sequentially, or in any desired order. Furthermore, the measurements may be determined using the magnetic sensors having different shapes, sizes, orientations, and/or distance from the magnetic source. In one embodiment, for example, AMR, GMR, and/or SMR sensors having different sizes and orientation may be used to measure the disturbances in the magnetic field caused by the blood flow.

Further, at step 910, variations in the plurality of measurements caused by magnetization-relaxation of the fluid flowing through the vessel may be determined based on a coupled model. As previously noted, the magnetic field measurements are significantly affected by the brief magnetization-relaxation of blood flowing away from the magnetic source. The coupled model accurately describes the behavior of magnetized blood based on determined relationships between the magnetization-relaxation of blood, the magnetic field measurements, and conservation of linear and angular momentum that governs the blood flow. An embodiment of the coupled model is described in detail with reference to FIGS. 6-7. Specifically, the coupled model aids in determining the variations in the magnetic field measurements caused by the magnetization relaxation of blood that are different from the variations caused by the flow of pulsatile blood through the blood vessel.

Moreover, at step 912, values of one or more desired parameters may be estimated based on the determined variations. Particularly, in one embodiment, one or more physiological parameters such as flow velocity and direction, blood pressure, heart rate, and oxygenation may be correlated with an amplitude of an output signal corresponding to the determined variations, for example, using equations 10 and 15. The estimated values of the physiological parameters, in turn, may be used to assess and/or monitor a pathological condition of the patient in real-time. For example, the blood flow parameters may be used to detect different anomalies such as hypovolemia, internal bleeding, cardiac output, and/or flow restrictions caused by atherosclerosis. Additionally, the blood flow parameters, for example, may also be used for post treatment monitoring for assessing flow restoration immediately after revascularization and for monitoring for post-vascularization thrombosis.

Further, at step 914, an audio alert and/or a visual alert may be generated when one or more values of the desired parameters are outside prescribed thresholds. As previously noted with reference to step 912, the physiological parameters corresponding to the patient may be continually monitored for assessing a pathological condition of the patient in real-time. Accordingly, if it is determined that one or more of the physiological parameters such as blood oxygenation, blood pressure, and/or heart rate has fallen below clinically prescribed thresholds, an audio and/or visual alert may be generated to alert a medical practitioner regarding the patient's condition. In certain embodiments, the alert message may additionally or alternatively be communicated via an email, a short messaging service (sms), and/or a popup to a remotely connected system such as the HIS or a selected mobile phone number to aid in providing prompt medical attention to the patient.

Embodiments of the present systems and methods, thus, allow for non-invasive and continual monitoring of one or more physiological parameters of a patient to aid in early detection of different anomalies. Particularly, the embodiments described herein present a coupled model that accurately defines behavior of pulsatile blood based on principles of magnetization-relaxation, magnetostatics, and conservation of momentum. The accurately defined behavior of blood may aid in efficient correlation of magnetic field measurements to the one or more physiological parameters for evaluating a health condition of the patient.

Additionally, the embodiments of the present system also disclose a low power, lightweight, low cost, portable, and non-invasive sensing device that does not need direct skin contact and is robust to body movements. Further, a miniature size and flexible nature of the sensing device allows for less stringent rules for placement of the sensor on a target region, thereby allowing for use in target regions such as the ankle that may not be serviceable using conventional monitoring devices. Moreover, use of an array of magnetic sensors in the sensing device allows for generation of stronger and redundant output signals to provide higher signal-to-noise ratio and improved robustness against stray magnetic fields. Further, the arrayed sensor design aids in simultaneous magnetic field measurements at a plurality of locations, thus providing more information that may be cohesively used to determine complex physiological parameters.

Although, the present description is disclosed with reference to accurately modeling a behavior of the blood using the coupled model and physiological monitoring of the patient based on the modeled behavior, alternative embodiments of the present methods and systems may find use in other medical and/or non-medical application areas. For example, certain embodiments of the present methods and systems may be used in modeling other magnetic fluids such as oil for use in non-destructive evaluation studies including detecting cracks in oil and gas pipelines and detecting bearing wear based on a coupled model that defines behavior of oil, gas, and/or bearing oil, respectively.

It may be noted that although specific features of various embodiments of the present systems and methods may be shown in and/or described with respect to only certain drawings and not in others, this is for convenience only. It is to be understood that the described features, structures, and/or characteristics may be combined and/or used interchangeably in any suitable manner in the various embodiments, for example, to construct additional assemblies and techniques. Furthermore, the foregoing examples, demonstrations, and process steps, for example, those that may be performed by the magnetic field modulator 114, the processing subsystem 128, and the alerting subsystem 142 may be implemented by a single device or a plurality of devices using suitable code on a processor-based system.

It should also be noted that different implementations of the present disclosure may perform some or all of the steps described herein in different orders or substantially concurrently, that is, in parallel. In addition, the functions may be implemented in a variety of programming languages, including but not limited to Python, C++, or Java. Such code may be stored or adapted for storage on one or more tangible, machine-readable media, such as on data repository chips, local or remote hard disks, optical disks (that is, CDs or DVDs), solid-state drives, or other media, which may be accessed by a processor-based system to execute the stored code.

While only certain features of the present disclosure have been illustrated and described herein, many modifications and changes will occur to those skilled in the art. It is, therefore, to be understood that the appended claims are intended to cover all such modifications and changes as fall within the true spirit of the present disclosure.

The invention claimed is:

1. A system for monitoring a subject, comprising:
a sensing device, comprising:
at least one magnetic source to generate a varying magnetic field;
an array of magnetic sensors disposed within a target region of the varying magnetic field to obtain a plurality of measurements corresponding to the varying magnetic field at a plurality of locations along a blood vessel;
a processing subsystem communicatively coupled to the sensing device, wherein the processing subsystem is to:
determine variations in the plurality of measurements caused by magnetization-relaxation of blood flowing through the blood vessel based on a coupled model using a moving mesh technique, wherein the coupled model defines a behavior of the blood in the varying magnetic field quantified as one or more physiological parameters based on magnetization-relaxation, bulk motion of the blood towards a determined gradient of the magnetic field, magnetostatics, and conservation of momentum, and wherein the moving mesh technique measures magnetization of the blood during an idle state and a flowing state and demagnetization of the blood flow away from the at least one magnetic source, the magnetization and demagnetization forming distortions in the magnetic field corresponding to the variations; and
estimate values of the one or more physiological parameters representative of variations in the plurality of measurements caused by pulsatile flow of the blood based on the determined variations, the estimated values of the one or more physiological parameters to trigger an alert when the estimated values are outside one or more prescribed thresholds.

2. The system of claim 1, wherein the array of magnetic sensors comprises one or more semiconducting magnetoresistance sensors.

3. The system of claim 2, wherein the at least one magnetic source comprises a plurality of magnets having interlaced north and south poles, and wherein the semiconducting magnetoresistance sensors are positioned at least one of (i) on top of the plurality of magnets or (ii) at a determined distance from the plurality of magnets.

4. The system of claim 1, wherein the array of magnetic sensors comprises at least one of a magnetoresistance sensor, a hall-effect sensor, an anisotropic magnetoresistance sensor, a giant magnetoresistance sensor, or a coil sensor.

5. The system of claim 1, further comprising a substrate having the magnetic source and the array of magnetic sensors disposed therein, wherein the substrate comprises at least one of a flexible substrate or a rigid substrate.

6. The system of claim 5, wherein the magnetic source and the array of magnetic sensors at least one of: are disposed on the substrate in one or more selected orientations or have one or more selected sizes.

7. The system of claim 5, wherein one or more magnetic sensors in the array of magnetic sensors are disposed on the substrate at one or more selected distances from the magnetic source.

8. The system of claim 1, further comprising a modulator operatively coupled to the sensing device to vary the magnetic field in at least one of a time domain or a spatial domain.

9. The system of claim 1, wherein the sensing device is communicatively coupled to the processing subsystem through at least one of a wired coupling means or a wireless coupling means.

10. The system of claim 1, further comprising an alerting subsystem, wherein the alerting subsystem generates the alert including at least one of an audio alert or a visual alert when values of one or more desired parameters are outside prescribed thresholds.

11. The system of claim 1, wherein the one or more desired parameters comprise at least one of a blood volume, a blood pressure, blood oxygenation, heart rate, or cardiac output.

12. The system of claim 11, wherein the processing subsystem is operatively coupled to a physiological monitoring device.

13. The system of claim 12, wherein the physiological monitoring device comprises at least one of a blood oxygenation monitor, a Doppler ultrasound system, or an optical heart rate monitor.

14. The system of claim 12, wherein the processing subsystem determines a pathological condition of the subject based on the values of one or more desired parameters and information determined using the physiological monitoring device.

15. A method for monitoring a subject, comprising:
providing a varying magnetic field that varies in at least one of a time domain or a spatial domain using at least one magnetic source comprising a plurality of magnets;
obtaining, from a sensing device, a plurality of measurements corresponding to the varying magnetic field at a plurality of locations along a blood vessel using one or more magnetic sensors disposed within a target region of the varying magnetic field;
determining, by a processing subsystem, variations in the plurality of measurements caused by magnetization-relaxation of the blood flowing through the blood vessel based on a coupled model using a moving mesh technique, wherein the coupled model defines a behavior of the blood in the varying magnetic field quantified as one or more physiological parameters based on magnetization-relaxation, bulk motion of the blood towards a determined gradient of the magnetic field, magnetostatics, and conservation of momentum, and wherein the moving mesh technique measures magnetization of the blood during an idle state and a flowing state and demagnetization of the blood flow away from the at least one magnetic source, the magnetization and demagnetization forming distortions in the magnetic field corresponding to the variations; and
estimating, by the processing subsystem, values of the one or more physiological parameters representative of variations in the plurality of measurements caused by pulsatile flow of the blood based on the determined variations, the estimated values of the one or more physiological parameters to trigger an alert when the estimated values are outside one or more prescribed thresholds.

16. The method of claim 15, wherein obtaining the plurality of measurements comprises simultaneously measuring the varying magnetic field at the plurality of locations along the vessel.

17. The method of claim 15, further comprising continually monitoring values of the one or more physiological parameters.

18. The method of claim 17, further comprising generating at least one of an audio alert or a visual alert when one or more values of the desired parameters are outside prescribed thresholds.

19. The method of claim 17, further comprising determining a pathological condition of the subject based on the values of one or more physiological parameters.

20. The method of claim 15, further comprising communicating the values of one or more physiological parameters to a system that is remotely connected to the array of magnetic sensors through at least one of a wired coupling means, or a wireless coupling means.

21. A non-transitory computer readable medium that stores instructions executable by one or more processors to perform a method for monitoring a subject, comprising:
providing a varying magnetic field that varies in at least one of a time domain or a spatial domain using at least one magnetic source comprising a plurality of magnets;
obtaining, from a sensing device, a plurality of measurements corresponding to the varying magnetic field at a plurality of locations along a blood vessel using one or more magnetic sensors disposed within a target region of the varying magnetic field;
determining, by a processing subsystem, variations in the plurality of measurements caused by magnetization-relaxation of the blood flowing through the blood vessel based on a coupled model using a moving mesh technique, wherein the coupled model defines a behavior of the blood in the varying magnetic field quantified as one or more physiological parameters based on of magnetization-relaxation, bulk motion of the blood towards a determined gradient of the magnetic field, magnetostatics, and conservation of momentum, and wherein the moving mesh technique measures magnetization of the blood during an idle state and a flowing state and demagnetization of the blood flow away from the at least one magnetic source, the magnetization and demagnetization forming distortions in the magnetic field corresponding to the variations; and
estimating, by the processing subsystem, values of the one or more physiological parameters representative of variations in the plurality of measurements caused by pulsatile flow of the blood based on the determined variations, the estimated values of the one or more physiological parameters to trigger an alert when the estimated values are outside one or more prescribed thresholds.

\* \* \* \* \*